United States Patent
Zha (10) Patent No.: US 11,512,202 B2
(45) Date of Patent: Nov. 29, 2022

(54) SOLID COLOR FILM, PREPARATION METHOD THEREOF, AND DISPLAY DEVICE

(71) Applicant: TCL CHINA STAR OPTOELECTRONICS TECHNOLOGY CO., LTD., Shenzhen (CN)

(72) Inventor: Bao Zha, Shenzhen (CN)

(*) Notice: Subject to any disclaimer, the term of this patent is extended or adjusted under 35 U.S.C. 154(b) by 233 days.

(21) Appl. No.: 16/626,330

(22) PCT Filed: Nov. 25, 2019

(86) PCT No.: PCT/CN2019/120482
§ 371 (c)(1),
(2) Date: Dec. 24, 2019

(87) PCT Pub. No.: WO2021/093009
PCT Pub. Date: May 20, 2021

(65) Prior Publication Data
US 2021/0324197 A1    Oct. 21, 2021

(30) Foreign Application Priority Data
Nov. 13, 2019   (CN) .......... 201911108585.8

(51) Int. Cl.
  *C09B 11/24*   (2006.01)
  *C09B 67/20*   (2006.01)
  (Continued)

(52) U.S. Cl.
  CPC .......... *C09B 11/24* (2013.01); *C07D 487/22* (2013.01); *C08K 5/3467* (2013.01); *C09B 67/0063* (2013.01); *G02B 5/223* (2013.01)

(58) Field of Classification Search
  CPC ..... C09B 11/24; C09B 67/0063; G02B 5/223; C07D 487/22; C08K 5/3467
  See application file for complete search history.

(56) References Cited

U.S. PATENT DOCUMENTS

| | | | |
|---|---|---|---|
| 2008/0023646 A1* | 1/2008 | Nau | C09D 11/50 250/458.1 |
| 2011/0092680 A1 | 4/2011 | Kim et al. | |
| 2019/0072806 A1* | 3/2019 | Zhang | G06F 1/3265 |

FOREIGN PATENT DOCUMENTS

| | | | |
|---|---|---|---|
| CN | 110407970 A | 11/2019 | |
| KR | 20180125752 A * | 11/2018 | ............. G01N 33/52 |
| WO | 2009128649 A2 | 10/2009 | |

OTHER PUBLICATIONS

Lin Yuan, Weiying Lin and Yanming Feng, A rational approach to tuning the pKa values of rhodamines for living cell fluorescence imaging, Org. Biomol. Chem., 2011, 9, 1723-1726. (Year: 2011).*
(Continued)

*Primary Examiner* — Bijan Ahvazi (57) ABSTRACT

The present invention provides a solid color film, a preparation method thereof and a display device. The solid color film includes a transparent substrate and a solid color material dispersed in the transparent substrate, and the solid color material includes a host structure formed of cucurbituril and a guest structure supported on the host structure and formed by bonding a carboxyl group-containing rhodamine-based dye and an aminoadamantane through a chemical bond, wherein the guest structure is bonded to the host structure through the adamantane to form a host-guest structure.

10 Claims, 2 Drawing Sheets reacting a carboxyl group-containing rhodamine dye with an amino adamantane to form a guest structure;  — S10 forming a host structure by using cucurbituril;  — S20 thoroughly stirring the guest structure and the host structure in a buffer to form a solid color material; and  — S30 uniformly dispersing the solid color material in a transparent resin, followed by baking to form the solid color film.  — S40

(51) Int. Cl.
*G02B 5/22* (2006.01)
*C07D 487/22* (2006.01)
*C08K 5/3467* (2006.01)

(56) References Cited

OTHER PUBLICATIONS

☐Pharmaceutical excipients☐ ☐Contemporary Encyclopedic Knowledge Dictionary☐ ☐Physical Organic Chemistry☐ ☐New J.Chem.☐ V.V.Vipin, ETC. Photonic band gap effect and dye-encapsulated enhanced fluorescene using monolithic colloidal photonic crystals.

* cited by examiner

```
reacting a carboxyl group-containing rhodamine dye with an     S10
amino adamantane to form a guest structure;

forming a host structure by using cucurbituril;                S20 thoroughly stirring the guest structure and the host structure S30
in a buffer to form a solid color material; and uniformly dispersing the solid color material in a transparent S40
resin, followed by baking to form the solid color film.
```

SOLID COLOR FILM, PREPARATION METHOD THEREOF, AND DISPLAY DEVICE

BACKGROUND OF INVENTION

Field of Invention

The present invention relates to a field of display technologies, and in particular, to a solid color film, a preparation method thereof, and a display device.

Description of Prior Art

Development of display technology is pursuit of color reproduction. Due to an increase in a variety of colors, color switching in TV pictures can be more natural, making picture hierarchy more distinct, showing more details and closer to reality. For a liquid crystal display, since a screen itself does not have a self-illuminating property, a color gamut can be improved by adjusting a backlight, and the color gamut is mainly realized by color filters of three primary colors (red, green, and blue). It is also possible to improve the color gamut by adjusting the backlight. Currently, there are two main ways to improve purity of the backlight in the industry, wherein one is using a blue LED combined with red and green fluorescent materials to constitute the backlight; and the other is using a quantum dot (QD) backlight technology.

In the two ways of improving the color gamut, since the three primary colors are not purified in the process of improving the color gamut, cyan and yellow orange lights are present, so the three primary colors emitted are not pure, and as the color gamut is raised, the light transmittance is decreased, such that it is difficult to achieve a brightness increase while achieving an improvement in the color gamut.

At present, rhodamine-based materials are often used in the industry to remove stray light. The rhodamine-based materials can absorb stray light other than the three primary colors, thereby improving the purity of the three primary colors. However, there is a shoulder peak at the left side of a maximum absorption peak of the rhodamine-based dye, and due to agglomeration of the rhodamine dye, absorption of the shoulder peak is enhanced, so that the rhodamine dye absorbs part of the blue and green light, thus impacting the brightness of the light.

When the rhodamine-based dye is used to improve the color gamut in the prior art, the absorption of the shoulder peak is enhanced due to the agglomeration of the rhodamine-based dye, so that the rhodamine-based dye absorbs part of the blue light and the green light, thus impacting the brightness of the light, causing technical problems.

SUMMARY OF INVENTION

A solid color film, including a transparent substrate and a solid color material dispersed in the transparent substrate, the solid color material including a host structure formed of cucurbituril and a guest structure supported on the host structure and formed by bonding a carboxyl group-containing rhodamine-based dye and an aminoadamantane through a chemical bond, wherein the guest structure is bonded to the host structure through the adamantane to form a host-guest structure.

Further, the rhodamine-based dye has a chemical structure as shown in formula (1), formula (2), formula (3), formula (4), or formula (5):

(1)

(2)

(3)

(4)

-continued (5)

wherein, in the formula (2), X⁻ is at least one of F⁻, Cl⁻, Br, $CF_3SO_3^-$, $CF_2HSO_3^-$, and $CFH_2SO_3^-$, and structures of $R_1$, $R_2$, $R_3$, $R_4$, and $R_5$ are independently selected from at least one of a linear alkane, a branched alkane, an alkoxy-containing linear or branched alkane, an ester-containing chain, an F-substituted alkane derivative, a conjugated compound in which an alkoxy group is bonded to an ester group, and a heterocyclic ring-containing compound;

in the formula (3), $R_1$ is at least one of F, Cl, Br, I and CN substituent groups; structures of $R_1$, $R_2$, $R_3$, and $R_4$ are independently selected from at least one of a linear alkane, a branched alkane, an alkoxy-containing linear or branched alkane, an ester-containing chain, an F-substituted alkane derivative, a conjugated compound in which an alkoxy group is bonded to an ester group, and a heterocyclic ring-containing compound;

in the formula (4), X— is at least one of F—, Cl—, Br—, CF3SO3-, CF2HSO3-, and $CFH_2SO_3^-$, and structures of $R_1$, $R_2$, $R_3$, and $R_4$ are independently selected from at least one of a halogen-substituted group, an amino group, a carboxyl group, a hydroxyl group, a sulfate group, an aldehyde group, an ester group, an acyl group, —COBr, a nitrile, a nitro group, =NH, =N, a benzene, and a phenol ring; and structures of $R_1$, $R_2$, $R_3$, and $R_4$ are independently selected from at least one of a linear alkane, a branched alkane, an alkoxy-containing linear or branched alkane, an ester-containing chain, an F-substituted alkane derivative, a conjugated compound in which an alkoxy group is bonded to an ester group, and a heterocyclic ring-containing compound;

in the formula (5), X— is at least one of F⁻, Cl⁻, Br⁻, $CF_3SO_3^-$, $CF_2HSO_3^-$, and $CFH_2SO_3^-$, and structures of $R_1$, $R_2$, and $R_3$ are independently selected from at least one of a halogen-substituted group, a carboxyl group, a hydroxyl group, a sulfate group, an aldehyde group, an ester group, an acyl group, —COBr, a nitrile, a nitro group, an amino group, a benzene, and a phenol ring; and structures of $R_1$, $R_2$, and $R_3$ are independently selected from at least one of a linear alkane, a branched alkane, an alkoxy-containing linear or branched alkane, an ester-containing chain, an F-substituted alkane derivative, a conjugated compound in which an alkoxy group is bonded to an ester group, and a heterocyclic ring-containing compound Further, the guest structure is synthesized by the following reaction scheme:

Further, the guest structure and the host structure are reacted by the following reaction scheme:

-continued

The present invention also provides a method of preparing a solid color film, including the following steps:

S10, reacting a carboxyl group-containing rhodamine dye with an amino adamantane to form a guest structure;

S20, forming a host structure by using cucurbituril;

S30, thoroughly stirring the guest structure and the host structure in a buffer to form a solid color material; and S40, uniformly dispersing the solid color material in a transparent resin, followed by baking to form the solid color film.

Further, the step S10 includes:

S11, placing the carboxyl group-containing rhodamine dye and the amino adamantane in dichloromethane to obtain a solution to be reacted;

S12, adding a catalyst to the solution to be reacted, wherein a carboxyl group in a benzene ring of the rhodamine dye and an amino group in the amino adamantane are reacted to obtain a reaction liquid after completion of a reaction;

S13, washing the reaction solution with saturated brine, and washing the reaction liquid with a saturated sodium bicarbonate solution, to remove an organic solvent in the reaction liquid; and S14, after washing the reaction solution with a detergent, subjecting the reaction solution to column chromatography to obtain the guest structure.

Further, the catalyst includes 4-dimethylaminopyridine and dicyclohexylcarbodiimide.

Further, the step S20 includes:

S21, dissolving propargyl-cucurbit [7] in dimethyl sulfoxide to obtain a mixed solution;

S22, adding a 11-azido-3,6,9-trioxadecane-1-amine modified nano microspheres, a buffer, and tris [(1-benzyl-1H-1,2,3-triazol-4-yl)methyl]amine to the mixed solution, and thoroughly stirring the mixture solution; and S23, centrifugally separating the stirred mixed solution to obtain the host structure.

Further, the buffer has a pH value of 7.1 to 7.5.

The present invention also provides a display device including a display screen and the above-mentioned solid color film, the solid color film being disposed on a light exiting side of the display screen.

Beneficial effects of the present invention are: forming a guest structure by reacting a rhodamine-based dye with adamantane, and using a host structure formed by cucurbituril to support the guest structure on the host structure to achieve the object of dispersing the rhodamine-based dye, so that when the color gamut of the display device is raised by the solid color film, the rhodamine-based dye is prevented from agglomerating to absorb part of the blue light and green light, thus improving the light-emitting brightness and display quality. In addition, the adamantane and the cucurbituril have high thermal stability, which is favorable for improvement of the thermal stability of the rhodamine dye, and facilitates a better use of the rhodamine dye in a film preparation.

BRIEF DESCRIPTION OF DRAWINGS

In order to more clearly illustrate the embodiments or the technical solutions of the existing art, the drawings illustrating the embodiments or the existing art will be briefly described below. Obviously, the drawings in the following description merely illustrate some embodiments of the present invention. Other drawings may also be obtained by those skilled in the art according to these figures without paying creative work.

DETAILED DESCRIPTION OF PREFERRED EMBODIMENTS

The following description of the various embodiments is provided to illustrate the specific embodiments of the invention. The spatially relative directional terms mentioned in the present invention, such as "upper", "lower", "before", "after", "left", "right", "inside", "outside", "side", etc. and the like, may be used herein for ease of description to describe one element or feature's relationship to another element(s) or feature(s) as illustrated in the figures which are merely references. The spatially relative terms are intended to encompass different orientations in addition to the orientation as depicted in the figures.

The present invention aims to solve the technical problems that in the prior art, the absorption of the shoulder peak is enhanced due to the agglomeration of the rhodamine-based dye when the rhodamine-based dye is used to improve the color gamut, so that the rhodamine-based dye absorbs part of the blue light and the green light, thus impacting the brightness of the light.

A solid color film 20 is provided, including a transparent substrate and a solid color material dispersed in the transparent substrate, the solid color material including a host structure formed of cucurbituril and a guest structure supported on the host structure and formed by bonding a carboxyl group-containing rhodamine-based dye and an aminoadamantane through a chemical bond, wherein the guest structure is bonded to the host structure through the adamantane to form a host-guest structure.

It should be noted that the host structure formed by cucurbituril is a macrocyclic host molecule, and the cucurbituril molecule has strong bonding with a variety of guests. The cucurbituril molecule is a barrel-shaped cyclic compound, and a cavity of the cucurbituril molecule is hydrophobic and open at both ends, being small at both ends and large at middle, such that it can encapsulate organic molecules, and the cavity is surrounded by carbonyl groups. Meanwhile, the carbonyl groups form bonding sites with cations, which enables the host structure to bond a charged portion of the cations or organic molecules through a hydrophobic action of the cavity, hydrogen bonding of the carbonyl group, and the like.

It should be noted that the host structure has a three-dimensional network structure, which is approximately spherical, and the rhodamine dye is modified by amino adamantane to form a guest structure of rhodamine-adamantane. The guest structure is located in an internal and on a surface of a network of the host structure, and the carbonyl group in the host structure is bonded to the cation on the adamantane in the guest structure, so that the guest structure is supported on the host structure to form a host-guest structure, which can avoid agglomeration of the rhodamine-based dye, thereby realizing monodispersion, so that when the color gamut of the display device is raised by the solid color film 20, the rhodamine-based dye is prevented from agglomerating to absorb part of the blue light and green light, thus improving the light-emitting brightness and display quality. In addition, the adamantane and the cucurbituril have high thermal stability, which is favorable for improvement of the thermal stability of the rhodamine dye, and facilitates a better use of the rhodamine dye in a film preparation.

Specifically, the rhodamine-based dye has a chemical structure as shown in formula (1), formula (2), formula (3), formula (4), or formula (5):

-continued wherein, in the formula (2), X⁻ is at least one of F⁻, Cl⁻, Br, $CF_3SO_3^-$, $CF_2HSO_3^-$, and $CFH_2SO_3^-$, and structures of $R_1$, $R_2$, $R_3$, $R_4$, and $R_5$ are independently selected from at least one of a linear alkane, a branched alkane, an alkoxy-containing linear or branched alkane, an ester-containing chain, an F-substituted alkane derivative, a conjugated compound in which an alkoxy group is bonded to an ester group, and a heterocyclic ring-containing compound;

in the formula (3), $R_1$ is at least one of F, Cl, Br, I and CN substituent groups; structures of $R_1$, $R_2$, $R_3$, and $R_4$ are independently selected from at least one of a linear alkane, a branched alkane, an alkoxy-containing linear or branched alkane, an ester-containing chain, an F-substituted alkane derivative, a conjugated compound in which an alkoxy group is bonded to an ester group, and a heterocyclic ring-containing compound;

in the formula (4), X⁻ is at least one of F⁻, Cl⁻, Br⁻, $CF_3SO_3^-$, $CF_2HSO_3^-$, and $CFH_2SO_3^-$, and structures of $R_1$, $R_2$, $R_3$, and $R_4$ are independently selected from at least one of a halogen-substituted group, an amino group, a carboxyl group, a hydroxyl group, a sulfate group, an aldehyde group, an ester group, an acyl group, —COBr, a nitrile, a nitro group, =NH, =N, a benzene, and a phenol ring; and structures of R1, R2, R3, and R4 are independently selected from at least one of a linear alkane, a branched alkane, an alkoxy-containing linear or branched alkane, an ester-containing chain, an F-substituted alkane derivative, a conjugated compound in which an alkoxy group is bonded to an ester group, and a heterocyclic ring-containing compound;

in the formula (5), X— is at least one of F⁻, Cl⁻, Br⁻, $CF_3SO_3^-$, $CF_2HSO_3^-$, and $CFH_2SO_3^-$, and structures of $R_1$, $R_2$, and $R_3$ are independently selected from at least one of a halogen-substituted group, a carboxyl group, a hydroxyl group, a sulfate group, an aldehyde group, an ester group, an acyl group, —COBr, a nitrile, a nitro group, an amino group, a benzene, and a phenol ring; and structures of $R_1$, $R_2$, and $R_3$ are independently selected from at least one of a linear alkane, a branched alkane, an alkoxy-containing linear or branched alkane, an ester-containing chain, an F-substituted alkane derivative, a conjugated compound in which an alkoxy group is bonded to an ester group, and a heterocyclic ring-containing compound.

When the rhodamine-based dye has a chemical structure as shown in any one of the formulas (2) to (5), in an embodiment, a chain length of the alkane may range from 1 to 30, and the heterocyclic ring-containing compound may be a five-membered heterocyclic compound, a six-membered heterocyclic compound, or a benzoheterocyclic compound; wherein the five-membered heterocyclic compound may be furan, thiophene, pyrrole, thiazole or imidazole; the six-membered heterocyclic compound may be pyridine, pyrazine, pyrimidine, or a pyridazine; and the benzoheterocyclic compound can be hydrazine, quinoline, pteridine, or acridine.

In an embodiment, when the rhodamine-based dye has a chemical structure as shown in the formula (1), the guest structure is synthesized by the following reaction scheme:

-continued

It should be noted that the carboxyl group-containing rhodamine dye is modified with amino adamantane, and in a dichloromethane (DCM) solvent, a carboxyl group in a bottom benzene ring of the rhodamine dye and an amino group in the adamantane can be reacted in a catalyst of 4-dimethylaminopyridine (DMAP) and dicyclohexylcarbodiimide (DCC) to form the guest structure of rhodamine-adamantane.

It should be noted that when the rhodamine-based dye has a chemical structure as shown in any one of the formulas (2) to (5), reaction conditions of the rhodamine-based dye and the aminoadamantane are the same as described above, and all of them are prepared by reacting a carboxyl group in a bottom benzene ring of the rhodamine dye and an amino group in the adamantane to form the guest structure of rhodamine-adamantane.

In an embodiment, the host structure has a structural formula as follows:

In an embodiment, the host-guest structure has a structural formula as follows:

the guest structure and the host structure are reacted by the following reaction scheme:

-continued

Specifically, the transparent substrate of the solid color film 20 may be made of a transparent resin, and the transparent resin may be selected from one or more of acrylic resin, dimethylaminoethyl methacrylate, butyl methacrylate, hydroxyethyl methacrylate, cyclohexyl methacrylate, and isooctyl methacrylate.

Figure 1:
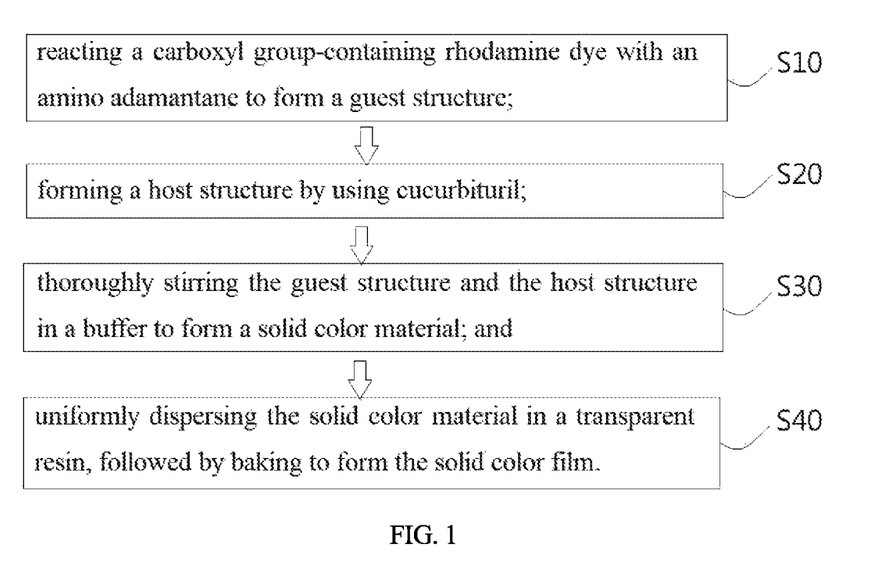
FIG. 1 is a schematic diagram showing steps of preparing a solid color film according to an embodiment of the present invention.

Based on the above-mentioned solid color film, the present invention also provides a method for preparing a solid color film, as shown in FIG. 1, including the following steps:

S10, reacting a carboxyl group-containing rhodamine dye with an amino adamantane to form a guest structure;

S20, forming a host structure by using cucurbituril;

S30, thoroughly stirring the guest structure and the host structure in a buffer to form a solid color material; and S40, uniformly dispersing the solid color material in a transparent resin, followed by baking to form the solid color film.

Specifically, the step S10 includes:

S11, placing the carboxyl group-containing rhodamine dye and the amino adamantane in dichloromethane to obtain a solution to be reacted;

S12, adding a catalyst to the solution to be reacted, wherein a carboxyl group in a benzene ring of the rhodamine dye and an amino group in the amino adamantane are reacted to obtain a reaction liquid after completion of a reaction;

S13, washing the reaction solution with saturated brine, and washing the reaction liquid with a saturated sodium bicarbonate solution, to remove an organic solvent in the reaction liquid; and S14, after washing the reaction solution with a detergent, subjecting the reaction solution to column chromatography to obtain the guest structure.

It should be noted that, in the step S11, the amino adamantane may be 1,4-butanediamine-adamantane, and a weight ratio of the rhodamine dye to the aminoadamantane may be 1:1.1. In the step S12, the rhodamine dye and the amino adamantane may be reacted at room temperature for 24 hours. In the step S14, the detergent may be n-hexane: dichloromethane.

In an embodiment, the catalyst includes 4-dimethylaminopyridine and dicyclohexylcarbodiimide.

Specifically, the step S20 includes:

S21, dissolving propargyl-cucurbit [7] in dimethyl sulfoxide to obtain a mixed solution;

S22, adding a 11-azido-3,6,9-trioxadecane-1-amine modified nano microspheres, a buffer, and tris [(1-benzyl-1H-1, 2,3-triazol-4-yl)methyl]amine to the mixed solution, and thoroughly stirring the mixed solution; and S23, centrifugally separating the stirred mixed solution to obtain the host structure.

It should be noted that, in step S22, the propargyl-cucurbituril [7] may have a particle diameter of 3 mm, the nano microspheres may be polymethyl methacrylate (PMMA) microspheres or polyphenylene ethylene (PS) microspheres, the buffer may include diammonium hydrogen phosphate, and have a pH value of 7.1 to 7.5, and the stirring may be performed at normal temperature for 24 hours.

In an embodiment, the buffer has a pH value of 7.2.

In an embodiment, the propargyl-cucurbituril [7], the nanospheres, the buffer, and the tris[(1-benzyl-1H-1,2,3-triazol-4-yl)methyl]amine have a volume ratio of is 1:12:10:10.

Specifically, in the step S40, a heating temperature may be 150° C., a heating time may be 30 minutes, and the solid color film 20 has a thickness of 0.1 to 1000 μm.

Figure 2:
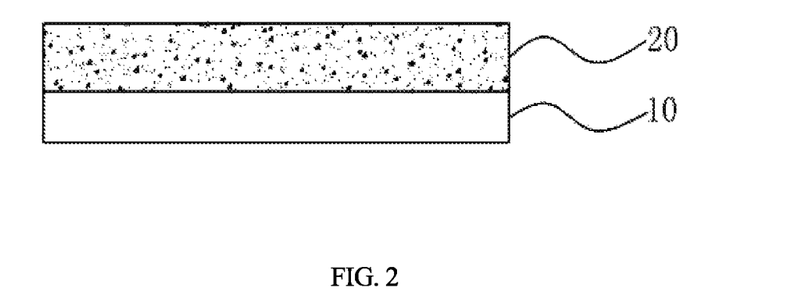
FIG. 2 is a schematic structural diagram of a display device according to an embodiment of the present invention.

The present invention further provides a display device. As shown in FIG. 2, the display device includes a display screen 10 and the solid color film 20, and the solid color film 20 is disposed on a light exiting side of the display screen 10.

The display device may be a liquid crystal display device, and the solid color film 20 may be disposed on a polarizer, an optical adhesive layer, or a color filter in the display device, to selectively absorb stray light, such as yellow orange light and cyan light, thereby increasing the color gamut of the display device.

Beneficial effects of the present invention are: forming a guest structure by reacting a rhodamine-based dye with adamantane, and using a host structure formed by cucurbituril to support the guest structure on the host structure to achieve a purpose of dispersing the rhodamine-based dye, so that when the color gamut of the display device is raised by the solid color film 20, the rhodamine-based dye is prevented from agglomerating to absorb part of the blue light and green light, thus improving the light-emitting brightness and display quality. In addition, the adamantane and the cucurbituril have high thermal stability, which is favorable for improvement of the thermal stability of the rhodamine dye, and facilitates a better use of the rhodamine dye in a film preparation.

While the invention has been described by way of example and in terms of the preferred embodiments, it is to be understood that the invention is not limited to the disclosed embodiments. To the contrary, it is intended to cover various modifications and similar arrangements. Therefore, the scope of the appended claims should be accorded the broadest interpretation so as to encompass all such modifications and similar arrangements.

What is claimed is:

1. A solid color film, comprising a transparent substrate and a solid color material dispersed in the transparent substrate, the solid color material comprising a host structure formed of cucurbituril and a guest structure supported on the host structure, wherein the guest structure is formed by bonding a carboxyl group-containing rhodamine-based dye and an amino adamantane through a chemical bond, and the guest structure is bonded to the host structure through an amino cation group of the rhodamine-based dye of the guest structure, and a carbonyl group on the cucurbituril in the host structure to form a host-guest structure.

2. The solid color film according to claim 1, wherein the rhodamine-based dye has a chemical structure as shown in formula (1), formula (2), formula (3), formula (4), or formula (5):

(1)

(2)

(3)

(4)

(5)

wherein, in the formula (2), X⁻ is at least one of F⁻, Cl⁻, Br, $CF_3SO_3^-$, $CF_2HSO_3^-$, and $CFH_2SO_3^-$, and structures of $R_1$, $R_2$, $R_3$, $R_4$, and $R_5$ are independently selected from at least one of a linear alkane, a branched alkane, an alkoxy-containing linear or branched alkane, an ester-containing chain, an F-substituted alkane derivative, a conjugated compound in which an alkoxy group is bonded to an ester group, and a heterocyclic ring-containing compound;

in the formula (3), $R_1$ is at least one of F, Cl, Br, I and CN substituent groups; structures of $R_1$, $R_2$, $R_3$, and $R_4$ are independently selected from at least one of a linear alkane, a branched alkane, an alkoxy-containing linear or branched alkane, an ester-containing chain, an F-substituted alkane derivative, a conjugated compound in which an alkoxy group is bonded to an ester group, and a heterocyclic ring-containing compound;

in the formula (4), X⁻ is at least one of F⁻, Cl⁻, Br⁻, $CF_3SO_3^-$, $CF_4HSO_3^-$, and $CFH_2SO3^-$, and structures of $R_1$, $R_2$, $R_3$, and $R_4$ are independently selected from at least one of a halogen-substituted group, an amino group, a carboxyl group, a hydroxyl group, a sulfate group, an aldehyde group, an ester group, an acyl group, —COBr, a nitrile, a nitro group, =NH, ≡N, a benzene, and a phenol ring; and structures of $R_1$, $R_2$, $R_3$, and $R_4$ are independently selected from at least one of a linear alkane, a branched alkane, an alkoxy-containing linear or branched alkane, an ester-containing chain, an F-substituted alkane derivative, a conjugated compound in which an alkoxy group is bonded to an ester group, and a heterocyclic ring-containing compound;

in the formula (5), X— is at least one of F⁻, Cl⁻, Br⁻, $CF_3SO_3^-$, $CF_2HSO_3^-$, and $CFH_2SO_3^-$, and structures of $R_1$, $R_2$, and $R_3$ are independently selected from at least one of a halogen-substituted group, a carboxyl group, a hydroxyl group, a sulfate group, an aldehyde group, an ester group, an acyl group, —COBr, a nitrile, a nitro group, an amino group, a benzene, and a phenol ring; and structures of $R_1$, $R_2$, and $R_3$ are independently selected from at least one of a linear alkane, a branched alkane, an alkoxy-containing linear or branched alkane, an ester-containing chain, an F-substituted alkane derivative, a conjugated compound in Which an alkoxy group is bonded to an ester group, and a heterocyclic ring-containing compound.

3. The solid color film according to claim 1, wherein the guest structure is synthesized by the following reaction scheme:

4. The solid color film according to claim 3, wherein the guest structure and the host structure are reacted by the following reaction scheme:

-continued

5. A display device, comprising a display screen and the solid color film according to according to claim 1, wherein the solid color film is disposed on a light exiting side of the display screen.

6. A method of preparing a solid color film, comprising the following steps:
S10, reacting a carboxyl group-containing rhodamine dye with an amino adamantane to form a guest structure;
S20, forming a host structure by using cucurbituril;
S30, thoroughly stirring the guest structure and the host structure in a buffer to form a solid color material; and
S40, uniformly dispersing the solid color material in a transparent resin, followed by baking to form the solid color film, and wherein the solid color material comprising a host structure formed of cucurbituril and a guest structure supported on the host structure, wherein the guest structure is formed by bonding a carboxyl group-containing rhodamine-based dye and an amino adamantane through a chemical bond, and the guest structure is bonded to the host structure through an amino cation group of the rhodamine-based dye of the guest structure, and a carbonyl group on the cucurbituril in the host structure to form a host-guest structure.

7. The method of preparing the solid color film according to claim 6, wherein the step S10 comprises:
S11, placing the carboxyl group-containing rhodanine dye and the amino adamantane in dichloromethane to obtain a solution to be reacted;

S12, adding a catalyst to the solution to be reacted, wherein a carboxyl group in a benzene ring of the rhodamine dye and an amino group in the amino adamantane are reacted to obtain a reaction liquid after completion of a reaction;

S13, washing the reaction solution with saturated brine, and washing the reaction liquid with a saturated sodium bicarbonate solution, to remove an organic solvent in the reaction liquid; and S14, after washing the reaction solution with a detergent, subjecting the reaction solution to column chromatography to obtain the guest structure.

8. The method of preparing the solid color film according to claim 7, wherein the catalyst comprises 4-dimethylaminopyridine and dicyclohexylcarbodiimide.

9. The method of preparing the solid color film according to claim 6, wherein the step S20 comprises:

S21, dissolving propargyl-cucurbit [7] in dimethyl sulfoxide to obtain a mixed solution;

S22, adding a 11-azido-3,6,9-trioxadecane-1-amine modified nano microspheres, a buffer, and tris [(1-benzyl-1H-1,2,3-triazol-4-yl)methyl]amine to the mixed solution, and thoroughly stirring the mixture solution; and S23, centrifugally separating the stirred mixed solution to obtain the host structure.

10. The method of preparing the solid color film according to claim 9, wherein the buffer has a pH value of 7.1 to 7.5.

\* \* \* \* \*